United States Patent [19]

Jones

[11] Patent Number: 5,264,628
[45] Date of Patent: Nov. 23, 1993

[54] PROCESS FOR PREPARING 5-(3-BUTYRYL-2,4,6-TRIMETHYL)-2-[1-(ETHOXYIMINO)PROPYL]-3-HYDROXYCYCLOHEX-2-EN-1-ONE

[75] Inventor: John D. Jones, Bury, England

[73] Assignee: Imperial Chemical Industries PLC, London, Great Britain

[21] Appl. No.: 885,999

[22] Filed: May 19, 1992

[30] Foreign Application Priority Data

Jun. 4, 1991 [GB] United Kingdom ............... 9111975

[51] Int. Cl.$^5$ ........................................ C07C 249/12
[52] U.S. Cl. ................................................ 564/256
[58] Field of Search ......................................... 564/256

[56] References Cited

FOREIGN PATENT DOCUMENTS 0085529 8/1983 United Kingdom ............... 564/256

OTHER PUBLICATIONS

Solomons, *Organic Chemistry*, 2nd Ed. New York, John Wiley and Sons 1980, pp. 478-482 and 506-515.
Kende et al., *Organic Reactions*, vol. 35, pp. 44-45, John Wiley & Sons, New York (1988).
Noller, *Chemistry of Organic Compounds*, p. 544, W. B. Saunders Co., Philadelphia (1957).

Primary Examiner—Richard L. Raymond
Assistant Examiner—Peter G. O'Sullivan
Attorney, Agent, or Firm—Joel G. Ackerman

[57] ABSTRACT

A process of preparing the compound of formula (I):

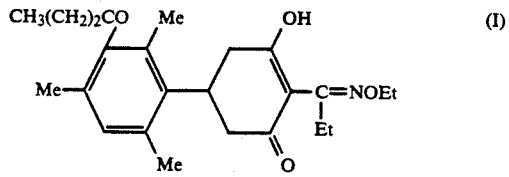

which comprises reacting butyryl chloride with the compound of formula (III):

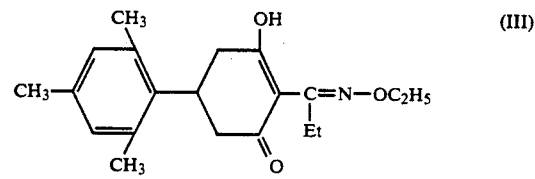

in the presence of a Friedel-Crafts catalyst, in an inert diluent.

5 Claims, No Drawings

PROCESS FOR PREPARING 5-(3-BUTYRYL-2,4,6-TRIMETHYL)-2-[1-(ETHOXYIMINO)PROPYL]-3-HYDROXYCYCLOHEX-2-EN-1-ONE

This invention relates to chemical processes.

European Patent No. 85529 discloses a class of 2-[1-(alkoxyimino)alkyl]-5-(substituted phenyl) cyclohexane-1,3-dione derivatives useful as selective herbicides.

A compound of this class, 5-(3-butyryl-2,4,6-trimethyl)-2-[1-(ethoxyimino)propyl]-3-hydroxycyclohex-2-en-1-one, having the structural formula (I), has been found to be particularly useful in the selective control of graminaceous weeds.

European Patent No. 85529 describes the preparation of compounds of this type (although the compound of formula (I) is not itself disclosed), by reaction of an alkoxyamine $R^2ONH_2$ (where $R^2$ is for example a lower alkyl group) with an intermediate of formula (II) where $R^3$ is, for example, a lower alkyl group, X is for example a lower alkyl or lower alkylcarbonyl group, and m is 3, 4 or 5.

The present invention provides an alternative process for preparation of the compound of formula (I).

According to the present invention, therefore, there is provided a process of preparing the compound of formula (I), which comprises reacting butyryl chloride with the compound of formula (III) in the presence of a Friedel-Crafts reaction catalyst, in an inert diluent. Preferably the Friedel-Crafts catalyst is anhydrous aluminium chloride. The aluminium chloride is used in an amount of from three to six molar proportions with respect to the compound (III), and preferably from 3.4 to 4.0 molar proportions. The butyryl chloride is used in an amount of from 1.0 to 4.0 molar proportions and preferably from 2.0 to 2.5 molar proportions with respect to the compound (III).

The diluent used in the process may be selected from those diluents known to be used in Friedel-Crafts reactions. It may be for example a hydrocarbon or a chlorinated hydrocarbon, or a nitro-hydrocarbon. Examples of diluents which may be used include aliphatic and alicyclic hydrocarbons, for example the mixture of aliphatic hydrocarbons sold under the trade name Isopar M, which has a boiling range of 210°-250° C., and cyclohexane. Chlorinated hydrocarbons include, for example, dichloromethane and tetrachloroethylene.

Nitro-hydrocarbons include, for example, nitrobenzene and nitromethane.

When using cyclohexane as the diluent, the reaction is preferably carried out at a temperature in the range from 5°-25° C. and more preferably in the range 10°-20° C. When using other diluents, the reaction temperature may range up to 45° C.

A preferred procedure for carrying out the process of the invention is to add compound (III) to cyclohexane at ambient temperature with stirring. Anhydrous aluminium chloride is then added to the slurry of compound III and the mixture cooled to 10° C. with stirring. The butyryl chloride, optionally diluted with the diluent for the reaction is then added over a period of time with stirring and cooling to maintain the temperature in the range of 10°-15° C. The reaction mixture is stirred for a period at 10° C., and then allowed to warm to ambient temperature while being stirred for a further period of up to 16 hours. When reaction is judged to be sufficiently complete, the reaction mixture is transferred gradually into an excess of dilute hydrochloric acid with stirring, the temperature of the mixture being maintained between 40° and 45° C. by cooling. When the transfer is complete, the mixture is stirred for a further period (for example of about 30 minutes) and the cyclohexane solution then separated and washed with water and if necessary aqueous sodium bicarbonate solution to remove butyric acid. The cyclohexane is then removed, for example by vacuum distillation, to give the product, compound (I), as an oil.

The order of addition of the reactants may be varied from that specified above. Such variations are illustrated in the Examples.

It is surprising that compound (I) can be prepared in high yield and quality by the process of the invention, given that Friedel-Crafts reactions often give products which require purification, for example by recrystallisation. This is the more surprising in that the starting material, compound (III), and the product, compound (I), are relatively labile compounds, and are readily converted into the corresponding oxazole derivatives (IV, R=H or nPrCO).

If desired, the compound (I) produced by the above process although of high quality, may be further purified by crystallisation from an anhydrous solvent. Such crystallisation has been described in Australian Patent Application No. PK 3569 of 1990. Preferred solvents for crystallising the compound (I) in the anhydrous form include low-boiling (e.g. up to a maximum boiling-point of 100° C.) hydrocarbons for example, cyclohexane, hexane, heptane, and mixed hydrocarbons. The compound (I) is dissolved by warming in the anhydrous solvent to a maximum temperature of less than 80° C., and then cooled, when the anhydrous crystalline form of compound (I) separates and is filtered off and dried under vacuum. The maximum temperature of 80° C. is specified because above this temperature the compound (I) is converted into the corresponding oxazole derivative (IV, R=PrCO). Solvents containing a hydroxy group should be avoided if the anhydrous crystalline form of compound (I) is required. Generally, it is preferred to prepare the anhydrous crystalline form of compound (I), since it is easier to formulate into herbicidal compositions, and is more convenient to handle and transport. If desired, however, compound (I) can be obtained in the form of its crystalline monohydrate, by crystallising the compound (I) obtained by the process of the invention from a solvent containing a hydroxy group, for example a lower alkanol, containing a small proportion of water. The crystalline form of compound (I) so obtained is the mono-hydrate, with a melting point of 30° C.; this may be dried in air. The following description illustrates the crystallisation of compound (I) in the anhydrous form, following the preparation of the compound by the process of the invention.

A preparation of compound (I) from compound (III) was carried out on a 0.1 molar scale, and the compound (I) isolated as described in Example 1 below. The compound (I) was obtained as a brown oil. In order to avoid the possibility of premature crystallisation of the product the temperature of this was not allowed to fall below 40° C. n-Heptane (235 ml) was added, and a proportion of this (about 100 ml) was then removed by distillation under reduced pressure (ca—180 mm Hg) to remove any traces of cyclohexane remaining from the reaction mixture. The solution which remained (about 29% w/w) was then cooled in an ice bath to 2°-3° C. for 1 to 2 hours. Nucleation occurred after 30-50 minutes.

The ice bath was then removed and the slurry left at room temperature overnight. Final crystallisation occurred on cooling the mixture to 2°-3° C. for 1-2 hours before filtration and washing with n-heptane (2×25 ml). The compound (I) was dried under vacuum at below 40° C. and was obtained as an off-white powder (36.6 g) of 97.3% purity.

The invention is illustrated by the following Examples.

EXAMPLE 1

This Example illustrates a preferred procedure for carrying out the process of the invention.

Compound (III), a dry powder (32.9 g, 100% wt, 0.1 mol) was slurried in cyclohexane (600 ml) at ambient temperature and stirred for 30 minutes. The suspension was cooled to 10° C., aluminium chloride (49.4 g, 0.37 mol) added in one portion and the mixture stirred for 5 minutes. n-Butyryl chloride (21.3 g, 100% wt, 0.2 mol) was added over a period of 15 minutes controlling the temperature at 10°-15° C. (exothermic). The reaction mixture was stirred at 10° C. for 30 minutes and for a further 16 hours while allowing the batch to rise to 20° C. The product slurry was drowned out into water (300 g) and 36% hydrochloric acid (180 g) while controlling the temperature between 40° C. and 45° C. The hydrolysis mixture was stirred for a further 30 minutes, allowed to settle and the phases separated. The cyclohexane layer was washed with water (300 g) and the phases separated. During the aqueous separations the temperature is held at 43°-45° C. to prevent the monohydrate of Compound (I) from crystallising. The cyclohexane is removed by vacuum distillation (150 mmHg) at a batch temperature of 40° C.-45° C. and a vacuum then applied to the stirred batch at 20°-25° C. for 1 hour to reduce the level of the remaining cyclohexane below 1.0% w/w.

Using this procedure, typical yields of 36-38 kg at 90-95% strength are obtained, which represents 90-95% of theoretical, based on the weight of Compound (III) used as starting material.

The following Tables 1 and 2 give the results obtained by carrying out the above procedure under various reaction conditions.

TABLE I

| Molar Ratios Compound III = 1.0 | | AlCl$_3$/ Compound (III) Hold Period | | nPrCOCl Addition | | Yield (%) |
|---|---|---|---|---|---|---|
| AlCl$_3$ | nPrCOCl | Time | Temp | Time | Temp | |
| 3.4 | 2.0 | 2 hours | 10° C. | 1.5 hr | 10-15° C. | 93 |
| 3.4 | 2.0 | 5 mins | 10° C. | 5 mins | 10° C. | 96 |
| 3.6 | 2.5 | 5 mins | 10° C. | 15 mins | 10° C. | 96 |
| 3.7 | 2.5 | 5 mins | 10° C. | 15 mins | 10-18° C. | 100 |
| 3.4 | 2.5 | 5 mins | 10° C. | 5 mins | 10-12° C. | 93 |
| 3.7 | 2.0 | 5 mins | 10° C. | 5 mins | 10-14° C. | 96 |
| 3.7 | 2.0 | 5 mins | 10° C. | 15 mins | 10-15° C. | 94 |
| 3.7 | 2.0 | 5 mins | 10° C. | 15 mins | 10-15° C. | 95 |
| 3.7 | 2.0 | 5 mins | 10° C. | 15 mins | 10° C. | 95 |
| 4.0 | 2.0 | 5 mins | 10° C. | 5 mins | 10-14° C. | 89 |
| 3.7 | 2.0 | 20 hours | 20° C. | 15 mins | 10-14° C. | 88 |
| 3.7 | 2.0 | 5 mins | 10° C. | 7 hours | 10-15° C. | 86 |
| 3.7 | 2.0 | 1 hour | 20° C. | 1 hour | 10° C. | 90 |
| 3.7 | 2.0 | 1 hour | 20° C. | 2 hours | 10-15° C. | 90 |
| 3.7 | 1.5 | 1 hour | 20° C. | 15 mins | 10° C. | 60 |
| 3.7 | 1.6 | 1 hour | 20° C. | 15 mins | 10° C. | 84 |

TABLE I-continued

| Molar Ratios Compound III = 1.0 | | AlCl$_3$/ Compound (III) Hold Period | | nPrCOCl Addition | | Yield (%) |
|---|---|---|---|---|---|---|
| AlCl$_3$ | nPrCOCl | Time | Temp | Time | Temp | |
| | | hour | | | | |

TABLE 2

| Molar Ratios Compound III = 1.0 | | AlCl$_3$/ Compound (III) Hold Period | | nPrCOCl Addition | | Yield (%) |
|---|---|---|---|---|---|---|
| AlCl$_3$ | nPrCOCl | Time | Temp | Time | Temp | |
| 3.4 | 2.0 | 5 mins | 20° C. | 3 mins | 20-45° C. | 52 |
| 3.4 | 2.0 | 5 mins | 15° C. | 5 mins | 10-15° C. | 97 |
| 3.4 | 2.0 | 5 mins | 15° C. | 5 mins | 10-15° C. | 97 |
| 3.4 | 2.0 | 5 mins | 15° C. | 10 mins | 15-20° C. | 95 |
| 3.4 | 2.0 | 30 mins | 30° C. | 15 mins | 30° C. | 58 |
| 3.4 | 2.0 | 1 hour | 30° C. | 15 mins | 10° C. | 86 |
| 3.8 | 2.0 | 1 hour | 30° C. | 15 mins | 15-20° C. | 73 |
| 3.4 | 2.0 | 2 hours | 20° C. | 15 mins | 20° C. | 92 |
| 3.4 | 2.0 | 3 hours | 15° C. | 5 mins | 10-15° C. | 95 |
| 3.4 | 2.0 | 5 mins | 15° C. | 30 mins | 15° C. | 99 |
| 3.4 | 2.0 | 2 hours | 10° C. | 30 mins | 10-15° C. | 93 |
| 3.4 | 2.0 | 2 hours | 10° C. | 1 hour | 10-15° C. | 92 |
| 3.4 | 2.0 | 5 mins | 15° C. | 2 hours | 10-15° C. | 80 |
| 3.4 | 2.0 | 2 hours | 10° C. | 3 hours | 10-15° C. | 98 |
| 3.4 | 2.0 | 2 hours | 10° C. | 4 hours | 10-15° C. | 98 |
| 3.4 | 2.0 | 2 hours | 10° C. | 5 hours | 10-18° C. | 88 |

EXAMPLE 2

This Example illustrates the process of the invention using a procedure alternative to that described in Example 1.

Powdered aluminium chloride (46.7 g, 0.35 mol) was slurried in dichloromethane (400 ml) at ambient temperature. n-Butyryl chloride (13.3 g, 100% wt, 0.125 mol) was added over ten minutes, controlling the reaction temperature at 18°-22° C., (slightly exothermic) and the mixture stirred for fifteen minutes. A solution of Compound (III) (32.9 g, 100% wt, 0.1 mol) in dichloromethane (50 ml) was added over 1.5 hours maintaining the reaction temperature at 20°-30° C. (exothermic). The reaction mixture was stirred at ambient temperature overnight. The thick slurry was transferred slowly into a mixture of water (300 g) and 36% hydrochloric acid (180 g) controlling the hydrolysis temperature at 20°-30° C. (exothermic). The hydrolysis mixture was stirred at ambient temperature for 0.5 hours and the layers separated. The following Table gives results for carrying out the above procedure under various reaction conditions.

TABLE 4

| Molar Ratios Relative to Compound III | | Yield of Compound (I) |
|---|---|---|
| AlCl$_3$ | nPrCOCl | |
| 2.5 | 1.25 | 66 |
| 3.0 | 1.25 | 83 |
| 3.2 | 1.25 | 97 |
| 3.5 | 1.25 | 97 |

TABLE 4-continued

| Molar Ratios Relative to Compound III | | Yield of Compound |
|---|---|---|
| AlCl$_3$ | nPrCOCl | (I) |
| 3.5 | 3.5 | 96 |
| 3.6 | 1.25 | 78 |
| 3.8 | 1.25 | 83 |
| 4.0 | 1.25 | 54 |
| 4.0 | 2.0 | 93 |
| 5.0 | 1.25 | 41 |

EXAMPLE 3

This Example illustrates the process of the invention using a further procedure alternative to that described in Example 1. Powdered aluminium chloride (45.4 g, 0.34 mol) was slurried in tetrachloroethylene (100 ml) at ambient temperature. n-Butyryl chloride (13.3 g, 100% wt, 0.125 mol) was added over ten minutes, controlling the reaction temperature at 18°-22° C. (slightly exothermic) and the mixture stirred for fifteen minutes. A solution of Compound (III) (32.9 g, 100% wt, 0.1 mol) in tetrachloroethylene (270 ml) was added over a period of 20 minutes maintaining the reaction temperature at 20° C. (exothermic). The purple slurry was stirred at ambient temperature overnight. The hydrolysis procedure was as described in Example 2.

The following Table gives results for carrying out the above procedure under various reaction conditions.

TABLE 5

| Compound III Addition | | Yield of |
|---|---|---|
| Time | Temp | Compound (I) |
| 20 mins | 20° C. | 90 |
| 20 mins | 20° C. | 96 |
| 45 mins | 25-35° C. | 93 |
| 1.5 hours | 25-30° C. | 97 |
| 1.5 hours | 10° C. | 96 |
| 3 hours | 20-25° C. | 80 |
| 6 hours | 20° C. | 52 |
| 30 mins | 40-45° C. | 77 |
| 1 hour | 40-45° C. | 83 |
| 3 hours | 40-45° C. | 74 |
| 2 mins | 25-45° C. | 85 |

EXAMPLE 4

This Example illustrates the process of the invention using a further procedure alternative to that described in Example 1. Powdered aluminium chloride (45.4 g, 0.34 mol) was slurried in tetrachloroethylene (240 g) at 18°-22° C. A solution of Compound (III) (32.9 g, 100% wt, 0.1 mol) and n-butyryl chloride (13.3 g, 100% wt, 0.125 mol) in tetrachloroethylene (405 g) was added over a period of 2.5 hours at a temperature of 20°-26° C. (exothermic). The reaction mixture was stirred at ambient temperature overnight. The hydrolysis procedure was as described in Example 1.

The yield of Compound (I) was 95.0%

The following Table gives the results of carrying out the above procedure under various reaction conditions.

| Compound III/nPrCOCl Addition | | |
|---|---|---|
| Time | Temp | Yield of Compound (I) |
| 40 mins | 20-30° C. | 91 |
| 2.5 hours | 20-26° C. | 95 |
| 4 hours | 20-25° C. | 76 |
| 1 hour | 35° C. | 86 |
| 1 hour | 40-45° C. | 85 |
| 5 hours | 40-45° C. | 65 |

EXAMPLE 5

This Example illustrates the process of the invention using a further procedure alternative to that described in Example 1. n-Butyryl chloride (37.8 g, 100% wt, 0.35 mol) was added to a slurry of aluminium chloride (46.9 g, 0.35 mol) in tetrachloroethylene (50 ml) at 0° C. over a period of fifteen minutes (exothermic). The resulting complex was added to a solution of Compound III (32.9 g, 100% wt, 0.1 mol) in tetrachloroethylene (350 ml) over a period of 1 hour at a reaction temperature of 20°-30° C. (exothermic). The reaction mixture was stirred at ambient temperature overnight. The hydrolysis procedure was as described in Example 2. Yield of Compound I based on Compound III used: 80.5%

The following Table shows the results of carrying out the above procedure under various reaction conditions.

| AlCl3-nPrCOCl Addition | | Yield of |
|---|---|---|
| Time | Temp | Compound (I) |
| 30 mins | 20-30° C. | 78 |
| 1 hour | 20-30° C. | 86 |
| 4 hours | 20-27° C. | 89 |
| 1 hour | 40-45° C. | 91 |

EXAMPLE 6

This Example illustrates the process of the invention using a further procedure alternative to that described in Example 1. n-Butyryl chloride (36.2 g, 100% wt, 0.34 mol) was added to a slurry of aluminium chloride (45.4 g, 0.34 mol) in cyclohexane (100 ml) at 0° C. over a period of fifteen minutes (exothermic). The resulting complex was added to a solution of Compound III (32.9 g, 100%, wt, 0.1 mol) in cyclohexane (300 ml) over a period of 5 hours at a reaction temperature of 20°-25° C. (exothermic). The reaction mixture was stirred at ambient temperature overnight. The hydrolysis procedure was as described in Example 1. Yield of Compound I was 94.0%.

The following Table gives the results obtained by carrying out the above procedure under various reaction conditions.

| AlCl3-nPrCOCl Addition | | |
|---|---|---|
| Time | Temp | Yield of Compound (I) |
| 25 mins | 20-30° C. | 98 |
| 1.75 hours | 20-30° C. | 86 |
| 5 hours | 20-25° C. | 97 |
| 5.75 hours | 35° C. | 89 |
| 25 mins | 45° C. | 87 |
| 2 hours | 45° C. | 73 |

CHEMICAL FORMULAE
(in description)

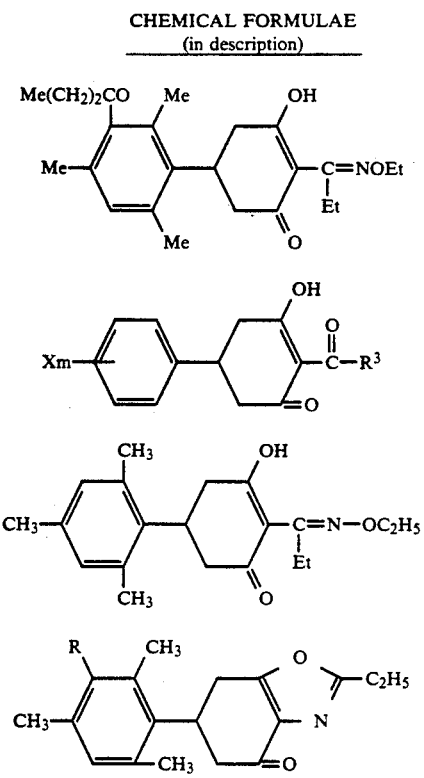

I claim:
1. A process of preparing the compound of formula (I):

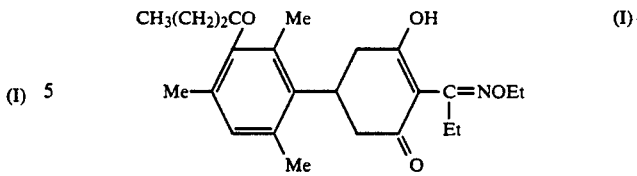

which comprises reacting butyryl chloride with the compound of formula (III):

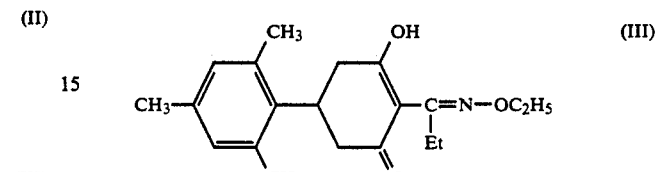

in the presence of a Friedel-Crafts catalyst, in an inert diluent.

2. A process as claimed in claim 1 wherein the Friedel-Crafts catalyst is aluminium chloride.

3. A process as claimed in claim 2 wherein the aluminium chloride is used in an amount of from three to four molar proportions with respect to compound (III).

4. A process as claimed in any of claims 1 to 3 wherein the diluent is an aliphatic or alicyclic hydrocarbon, or a chlorinated aliphatic hydrocarbon.

5. A process as claimed in any of claims 1 to 4 wherein the reaction of the claims 1 to 4 wherein the reaction of the butyryl chloride with the compound of formula (III) is carried out at from 10° to 45° C.

* * * * *